United States Patent
Knuebel et al.

(10) Patent No.: US 11,857,332 B2
(45) Date of Patent: Jan. 2, 2024

(54) DETERMINATION OF A DEGREE OF ELONGATION OF HAIR USING A NIR SENSOR

(71) Applicant: Henkel AG & Co. KGaA, Duesseldorf (DE)

(72) Inventors: Hans Georg Knuebel, Duesseldorf (DE); Lucile Bonnin, Berlin (DE); Astrid Kroos, Monheim (DE); Annika Koenen, Grevenbroich (DE); Erik Schulze Zur Wiesche, Bielefeld (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 624 days.

(21) Appl. No.: 17/055,024

(22) PCT Filed: Apr. 26, 2019

(86) PCT No.: PCT/EP2019/060727
§ 371 (c)(1),
(2) Date: Nov. 12, 2020

(87) PCT Pub. No.: WO2019/219350
PCT Pub. Date: Nov. 21, 2019

(65) Prior Publication Data
US 2021/0204865 A1      Jul. 8, 2021

(30) Foreign Application Priority Data

May 16, 2018   (DE) .................... 10 2018 207 557.3

(51) Int. Cl.
*A61B 5/107*   (2006.01)
*A61B 5/00*    (2006.01)
(Continued)

(52) U.S. Cl.
CPC ............ *A61B 5/448* (2013.01); *A45D 44/005* (2013.01); *A61B 5/0075* (2013.01); *G01N 21/359* (2013.01); *A61B 2560/0223* (2013.01)

(58) Field of Classification Search
CPC ........ A61B 5/448; A61B 5/107; A61B 5/0075
(Continued)

(56) References Cited

U.S. PATENT DOCUMENTS

| 6,993,851 B2 * | 2/2006 | Cohen ...................... G01B 3/18 |
| | | 33/784 |
| 7,110,117 B2 * | 9/2006 | Grossinger ............ G01N 21/84 |
| | | 356/402 |

(Continued)

FOREIGN PATENT DOCUMENTS

| DE | 102016225674 A1 | 7/2017 |
| DE | 102016212202 A1 | 1/2018 |
| EP | 1629775 A1 | 3/2006 |

OTHER PUBLICATIONS

EPO, International Search Report issued in International Application No. PCT/EP2019/060727, dated Jul. 10, 2019.
(Continued)

*Primary Examiner* — George B Bennett
(74) *Attorney, Agent, or Firm* — Lorenz & Kopf, LLP

(57) ABSTRACT

An arrangement for determining a degree of stretching of hair is provided. The arrangement includes a detection unit for detecting hair characteristics and an evaluation unit for evaluating the detected hair characteristics and for determining the degree of elongation of hair based on the detected hair characteristics. The detection unit contains a near-infrared sensor, and is configured to irradiate a hair sample with electromagnetic waves in the infrared range and to detect an absorbance of the hair sample in a wavelength range from about 800 to about 2500 nm. The acquisition unit is configured to generate an absorption spectrum of the hair
(Continued)

sample in the wavelength range of from about 800 to about 2500 nm and provide it to the evaluation unit and the evaluation unit is configured to compare the generated absorption spectrum with a calibration model and to determine a degree of elongation of the hair sample.

15 Claims, 4 Drawing Sheets

(51) Int. Cl.
   *A45D 44/00* (2006.01)
   *G01N 21/359* (2014.01)
(58) Field of Classification Search
   USPC .......................................................... 33/512
   See application file for complete search history.

(56) References Cited

U.S. PATENT DOCUMENTS

| | | | | |
|---|---|---|---|---|
| 8,611,588 | B2 * | 12/2013 | Kang ................... | A61B 5/448 |
| | | | | 382/128 |
| 10,311,575 | B2 * | 6/2019 | Stofel ................... | G06V 40/16 |
| 10,918,328 | B2 * | 2/2021 | Mueller ............... | A61B 5/0082 |
| 10,955,344 | B2 * | 3/2021 | Knuebel .............. | A61B 5/0071 |
| 2015/0082553 | A1 * | 3/2015 | Landa .................. | G01J 3/502 |
| | | | | 8/406 |
| 2019/0192067 | A1 * | 6/2019 | Knuebel .............. | G01J 3/0272 |
| 2019/0350515 | A1 | 11/2019 | Mueller et al. | |
| 2021/0121123 | A1 * | 4/2021 | Knuebel .............. | A61B 5/7264 |
| 2021/0267459 | A1 * | 9/2021 | Knuebel .............. | G01N 21/255 |

OTHER PUBLICATIONS

Jachowicz: "Hair damage and attempts to its repair", Journal of the Society Cosmetic Chemists, Society of Cosmetic Chemists, US, vol. 38, 1987, pp. 263-286.

Kreplak et al.: "New Aspects of the (alpha)-Helixn to (beta)-Sheet Transition in Stretched Hard (alpha)-Keratin Fibers", Biophysical Journal, Amsterdam, vol. 87, 2004, pp. 640-647.

Zoccola et al.: "Characterisation of keratin biomass from butchery and wool industry wastes", Journal of Molecular Structure, Amsterdam, vol. 938, 2009, pp. 35-40.

Antunes et al.: "Insights on the mechanical behavior of keratin fibrils", International Journal of Biological Macromolecules, Portugal, vol. 89, 2016, pp. 477-483.

* cited by examiner

DETERMINATION OF A DEGREE OF ELONGATION OF HAIR USING A NIR SENSOR

CROSS-REFERENCE TO RELATED APPLICATION

This application is a U.S. National-Stage entry under 35 U.S.C. § 371 based on International Application No. PCT/EP2019/060727, filed Apr. 26, 2019, which was published under PCT Article 21 (2) and which claims priority to German Application No. 10 2018 207 557.3, filed May 16, 2018, which are all hereby incorporated in their entirety by reference.

TECHNICAL FIELD

The present disclosure relates to a device for determining a degree of elongation of hair, a method for determining the degree of elongation of hair, and a computer program product adapted to perform the steps of such method when executed on a corresponding device.

BACKGROUND

When hair is treated with cosmetic products, the effect of the product, e.g. the intensity of a coloring, can depend very much on the damage to the hair.

Hair can be damaged by natural or artificial processes. Both external and internal hair damage can be relevant for the effect of a product. In general, hair can be damaged due to chemical or physical processes or due to mechanical effects.

Natural processes can include, for example, a combined (e.g. simultaneous) action of UV light and oxygen ($O_2$) on the hair. The artificially induced processes may include, for example, the application of hair dyes (also known as coloring), bleaching, and/or the creation of a permanent wave.

In addition to desired cosmetic effects, such as a lightening of the hair, this can also cause severe damage to the hair, for example when using oxidizing agents.

The resulting type of damage is called oxidative damage and is caused by the application of coloring, bleaching, permanent waves and by environmental influences (UV+ $O_2$). This damage is caused by the oxidation of the amino acids cystine and cysteine, which are common in hair, to cysteic acid.

Cystine can form intermolecular disulfide bridges (also known as S-S bridges) in the hair, so cystine is extremely important for the mechanical stability of the hair.

The oxidation of these bridges to cysteic acid can destroy the mechanical stability of the hair and even lead to complete hair breakage if used several times. However, macroscopically perceptible, e.g. tactile, properties of the hair, such as surface roughness, can be negatively influenced. The results of cosmetic treatments, especially damaging procedures, can also be massively changed at an early stage of damage compared to the results with undamaged hair.

Besides this oxidative damage, reductive damage to the hair is also possible. This occurs in cosmetic procedures that use reducing agents. These are, for example, perms or straighteners containing reducing agents such as thioglycolic acid or sulfite. These ingredients serve to open the disulfide bridges of cysteine to reshape the hair. The following sulfur species are formed: R—S—H (thiols), R—S—$SO_3$—, (colored salts, after sulfite treatment), R—S—S—CH2COO— (disulfides with thiglycolate units, after thioglycolate treatment).

Furthermore, as a mostly mechanical damage, a degree of stretching of hair is a relevant parameter, especially in case of irreversible overstretching (i.e. an overstretching exceeding about 10% of the unstretched length, measured e.g. at a relative humidity of a hair sample of about 45%), in order to be able to estimate the effect of care and/or treatment products on the hair in advance or even to select suitable products.

In an academic and industrial environment, a researcher or developer may have a variety of physical, chemical-analytical and/or biophysical methods at his disposal to determine the degree of internal and external damage to hair. Conventional chromatographic methods are used here, such as high-performance liquid chromatography (HPLC) after a complex acidic hydrolytic digestion of the hair sample. As a rule, such procedures are expensive in terms of equipment and are usually not usable by end users or consumers because they simply do not have access to them.

Harmful cosmetic treatments, such as hair coloring, heat treatments, permanent waves, or oxidative procedures such as bleaching, and many others, are typically carried out in the private sector or in the field of commercial services to the end consumer. Although performing another damaging procedure on pre-damaged hair can lead to catastrophic results or even complete hair breakage, up to now there was no simple way to determine the degree of stretching of the hair.

Furthermore, there are many different hair treatment products on the market which are designed to improve different hair properties or parameters, such as shine. In many cases, however, the user of such products is not aware of the damage to the hair. This can lead to the user resorting to products that are less suitable in his case and being dissatisfied with their effectiveness after use.

Therefore, determining a degree of stretching of the hair can be of great importance. It can also be advantageous to offer a product tailored to individual needs.

BRIEF SUMMARY

Arrangements and methods for determining a degree of elongation of hair are provided. In an exemplary embodiment, an arrangement for determining a degree of elongation of hair includes a detection unit and an evaluation unit. The detection unit is for detecting hair characteristics. The evaluation unit is for evaluating the detected hair characteristics and for determining a degree of elongation of hair based on the detected hair characteristics. The detection unit includes a near infrared sensor, NIRS, and is configured to irradiate a hair sample with electromagnetic waves in the infrared region and to detect an absorbance of the hair sample in a wavelength range from about 800 to about 2500 nm. The detection unit is configured to generate an absorption spectrum of the hair sample in the wavelength range from about 800 to about 2500 nm and to provide the absorption spectrum to the evaluation unit. The evaluation unit is configured to compare the absorption spectrum with a calibration model and to determine a degree of elongation of the hair sample based on the absorption spectrum and the calibration model.

In an exemplary embodiment, a method for determining a degree of elongation of hair. The method includes irradiating a hair sample with electromagnetic waves in an infrared range; detecting light emitted by the hair sample; measuring an absorbance of the hair sample in a wavelength range from about 800 to about 2500 nm; generating an absorption spectrum of the hair sample in a wavelength range from about 800 to about 2500 nm; and matching the absorption spectrum with a calibration model and determining the degree of elongation of hair based on the absorption spectrum and the calibration model.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It can be regarded as the task of the present disclosure to simplify the determination of a degree of stretching of hair, especially about the expenditure of apparatus and time.

This task is solved with the characteristics of independent claims. Further developments of the present disclosure result from the dependent claims and from the following description.

The present disclosure is based, inter alia, on the following findings: It was recognized that the overstretching of hair (the degree of stretching) is a relevant cosmetic parameter and that this degree of stretching can be detected with very little effort using near infrared sensors. This allows a non-mechanical and non-contact determination of the degree of stretching of hair. In particular, the degree of strain can be determined in a wavelength range of the near infrared (generally in a wavelength range of from about 780 to about 3000 nm), which allows the use of a near-infrared sensor with little equipment.

Human hair includes the dominant elements of cuticle and cortex cells. In addition to amorphous components, the cortex cells contain complex fibrillar structures that give the hair its mechanical stability. The basic building blocks of this complex fiber hierarchy are so-called α helices as secondary structure. Besides the α helices, so-called β folding structures are the most common form of secondary structures. In relation to the length per amino acid unit, α helices have a much more compact design compared to the β folding structures. The length of the α helices is about 0.15 nm per amino acid, while in the leaflet structure, about 0.35 nm is available per amino acid, which corresponds to a factor of well over about 2. During mechanical stretching of hair, a transformation of α helices into β leaflet structures can be observed. This represents a transformation process of existing structural elements and changes the structure of hair, which can be detected in an absorption spectrum of a hair sample in the infrared range.

According to one aspect, an arrangement for determining a degree of stretching of hair is given. The arrangement has an acquisition unit for acquiring hair characteristics and an evaluation unit for evaluating the acquired hair characteristics and determining the degree of elongation of hair based on the acquired hair characteristics. The detection unit contains a near infrared sensor, NIRS and is designed to irradiate a hair sample with electromagnetic waves in the infrared range and to detect an absorption coefficient of the hair sample in a wavelength range from about 800 to about 2500 nm. The acquisition unit is further designed to generate an absorption spectrum of the hair sample in the wavelength range from about 800 to about 2500 nm and provide it to the evaluation unit. The evaluation unit is designed to match the absorption spectrum with a calibration model and to determine a degree of elongation of the hair sample based on the absorption spectrum and the calibration model.

It was recognized that an absorption spectrum changes depending on the structure of hair and that the absorption spectrum in a wavelength range from about 800 to about 2500 nm (including these limits) is particularly important for determining a degree of elongation or mechanical overstretching of hair. The oscillation frequency and thus also the absorption spectrum of overstretched hair changes due to its structure. Over-expansion converts α helices into 13 leaflet structures, which changes the absorption spectrum.

Furthermore, it was recognized that an absorption spectrum of a hair sample can be detected and/or generated with a near-infrared sensor in the wavelength range from about 800 nm to about 2500 nm, and that the absorption spectrum in this wavelength range contains information about the degree of elongation of hair. In particular, the degree of stretching of hair can be determined in a wavelength range below about 3000 nm. This makes it possible to use near-infrared sensors that require little equipment. It is not necessary to fall back on much more complex sensors for the middle or far infrared range.

For the purposes of this description, near infrared (NIR) is defined as electromagnetic waves with a wavelength between about 780 nm and about 3000 nm (both inclusive). As described elsewhere in this document, certain smaller wavelength ranges are selected from this wavelength range to create an absorption spectrum of a hair sample and to infer the internal structure of the hair sample from this spectrum.

In the wavelength range between about 800 and about 2500 nm, harmonics of α helices and β-folded structures can be detected, which are an indicator for the degree of stretching of hair. In particular, the wavelength range between about 2000 and about 2500 nm, further especially between about 2000 and about 2350 nm, can be used to determine the absorption spectrum and to use it to determine the degree of strain. The considered wavelength range can be called the relevant wavelength range.

Harmonics of the α-helices can especially occur at one of the wavelengths from a first group of about 2012 nm, about 2056 nm, about 2168 nm, about 2183 nm, about 2206 nm, about 2293 nm, about 2345 nm. Harmonics of the β-pleated structures can especially occur at one of the wavelengths from a second group of about 2055 nm, about 2166 nm, about 2208 nm, about 2297 nm, about 2343 nm. The respective absorption coefficient of the hair sample at one wavelength from each of the two groups above can indicate how high the proportion of α helices and β-folded structures is in the hair sample.

Of course, the entire absorption spectrum over more than one wavelength value from each of the two groups above can also be used to determine the degree of strain. The range of the absorption spectrum used corresponds to the relevant wavelength range mentioned above.

In a calibration model, the absorption spectra of hair samples can be stored in the relevant wavelength range with different degrees of strain. Each hair sample and absorption spectrum is assigned a degree of elongation and the degree of elongation of the absorption spectrum from the calibration model that is qualitatively and/or quantitatively most similar to the absorption spectrum of the examined hair sample is assigned to the examined hair sample.

In particular, the acquired absorption spectrum of the hair sample in the relevant wavelength range is compared with the relevant wavelength range of the absorption spectra of the calibration model.

Stretch can be specified as the ratio of the length of a stretched hair to an unstretched hair.

Here the elongation is a dimensionless specification. If hair is stretched only within the fully reversible range (typically up to from about 3% to about 5% of its original length, i.e. unstretched length), it will always return to its original length after stretching. Only when the hair is stretched beyond the reversible range (from approx. 10% to about 15% stretching, the partially irreversible transformation of α-helices into β-pleated structures sets in, from approx. 25% the hair starts to tear), the hair will not completely return to the unstretched length, because an irreversible transformation of α-helices into β-pleated structures takes place. Different degrees of elongation can be specified as degrees of elongation. The scale from not stretched to tearing a hair can be divided into two or more stretching degrees.

For example, the following degrees of elongation can be used: not elongated, slightly elongated, strongly elongated, multiple strongly elongated. To determine the strain levels in the calibration model, other chemical or physical and biophysical methods can be used.

The evaluation unit can be a processor or a computer that implements and executes signal processing algorithms to determine the absorption spectrum of the hair sample based on the signals detected by the NIR sensor.

A hair sample can be a single hair, but preferably contains a number of individual hairs to increase the intensity of the light emitted by the hair sample as an inversion of the light absorbed by the hair sample (or the amount of emitted light relative to the emitted light) compared to a single hair. For example, hair can be examined non-destructively by pointing the detection unit at a person's scalp hair. In other words, the hair can be examined without having to cut it off.

The absorption spectrum can be determined from the light emitted by the hair sample. A spectrum of light is understood to be the absorption of light over the wavelength. The spectrum can be a continuous indication of the absorption of light in a wavelength range from a lower value to an upper value. This continuous indication describes the degree of absorption of light over the wavelength and has a characteristic curve for the structure of the individual hairs of the hair sample.

The near infrared sensor makes it possible to use methods of near infrared spectroscopy. These methods allow direct, non-destructive testing of the structure of hair without time-consuming sample preparation and without changing or destroying the structure of the hair by analysis.

This can enable results to be achieved more quickly. In addition, it may be possible to subject the hair to further treatments after the measurement, so that multiple applications or examinations can be carried out on one hair sample (for example in the form of a strand of hair).

In addition, it may be possible to perform relatively easy measurements at different hair positions (e.g. hair close to the scalp and hair removed from the scalp), for example directly on the head, without having to take the hair sample.

Near infrared spectroscopy can be used, for example, when sample preparation is difficult or impossible and a large number of samples have to be analyzed in a short time, e.g. in a pharmaceutical production for batch release or for measurements on skin or other biological objects.

Near-infrared spectroscopy is based on the measurement of spectral absorption by vibrational excitation of chemical bonds or structures of the hair sample. Depending on the type of bond or structure, absorption can occur at different wavelengths. As a rule, the absorption can follow Lambert-Beer's law and thus be proportional to a concentration of a component responsible for the absorption. Superimposed absorptions are additive, so that a quantification based on the absorption spectra is possible.

However, these absorptions can be overtones (e.g. in the NIR range) or combination oscillations. This can make it difficult to assign individual absorption wavelengths.

For this reason, chemometric methods can be used for the evaluation of the spectra and especially for the quantitative evaluation, to use the calibration model as a starting point for assigning a damage category.

NIR spectroscopy can also be suitable for measurements on hair because near-infrared radiation not only analyzes the surface of the hair, but because of the small absorption cross sections for near-infrared radiation (e.g. compared to light in the visible wavelength range) the hair can be at least partially penetrated and the internal condition of hair is also taken into account, which can be particularly relevant for determining a degree of elongation.

An evaluation of the spectra can be done by employing a calculation model, which can be developed in a calibration and validation phase using a sufficiently large collective of comparison spectra. For this purpose, it may be necessary to have reference values of the characteristics to be calibrated for all spectra.

The calculation model can be an artificial system that learns, for example, from the calibration hair samples and can generalize them after the learning phase is completed. This means that the examples are not simply learned by heart, but patterns and regularities in the learning data are recognized. Different approaches can be followed for this purpose. For example, supervised learning, semi-supervised learning, unsupervised learning, reinforced learning and/or active learning can be used, especially in combination with so-called deep learning methods. Supervised learning can, for example, take place using an artificial neural network (such as a recurrent neural network) or a support vector machine. Unsupervised learning can also take place by employing an artificial neural network (e.g. an autoencoder), decision trees or by using ensemble methods (e.g. so-called decision tree ensembles).

Spectra can basically be measured in transmission or reflection. Reflection detects the electromagnetic waves reflected from a sample and transmission detects the electromagnetic waves passing/transmitting the sample. For the purposes of this description, reflected or passing/transmitting electromagnetic waves are referred to as emitted electromagnetic waves or emitted light.

The absorption spectrum is generated by comparing or subtracting the electromagnetic waves detected by the detection unit (corresponding to the light emitted by the hair sample) with the initially emitted electromagnetic waves. The intensity over the wavelength represents the spectrum. The difference in intensity over wavelength between the emitted NIR light and the detected NIR light represents the absorption spectrum.

According to one design form, the evaluation unit is designed to match a curve of the absorption spectrum of the hair sample with a plurality of absorption spectra from the calibration model.

The calibration model can be available in a local memory of the evaluation unit. Alternatively, the evaluation unit can access an external data storage unit and retrieve the calibration model data for temporary use. This allows the calibration model to be kept at a central location and changed if necessary. Thus the (decentralized) evaluation unit always has a current data set of the calibration model available.

According to another version, the acquisition unit is designed to acquire or maintain a moisture level of the hair sample and to provide the moisture level to the evaluation unit, and the evaluation unit is designed to consider the moisture level of the hair sample when comparing the generated absorption spectrum with the calibration model.

The moisture content of the hair sample can be entered by a user or recorded by a sensor. This sensor can be part of the acquisition unit.

It has been found that stretched or overstretched hair changes its moisture or water content. This also changes the absorption spectrum of the hair. If the hair is exposed to an external source of moisture, such as high humidity or rain, this can influence the absorption spectrum in the wavelength range mentioned and on the associated degree of elongation. To eliminate the influence of moisture on the measurement result, the degree of moisture of the hair sample is considered.

To indicate the degree of humidity, for example, an indication of the air humidity may be sufficient. For example, humidity can be given as relative humidity, which is expressed in weight % and indicates the weight ratio of an instantaneous water vapor content to a maximum possible water vapor content in the air at the current temperature. The degree of moisture can also be expressed as the weight of water as a percentage of the total weight of the wet hair sample (weight of hair+weight of water). Simplified, the degree of moisture can then be indicated, for example, as one of several levels: slightly moist, moist, wet, very wet.

According to another version, the evaluation unit is designed to assign a damage category to the hair sample based on the comparison of the generated absorption spectrum with the calibration model.

The known and available absorption spectra of hair samples can be part of the calibration model. For example, the calibration model can be created based on a plurality of calibration hair samples, whereby a calibration spectrum is recorded for each individual calibration hair sample (as also described above for generating the spectrum of the hair sample to be examined) and the calibration hair sample is examined for damage using other independent analytical methods, and the damage thus determined is assigned to the calibration hair sample.

By comparing the spectra of the calibration hair samples with the spectrum of the hair sample to be tested, the degree of elongation for the latter can be determined. This adjustment can consider the shape of the spectrum and/or its intensity. Taking the shape into account can also provide a hit during the comparison if the structure of the hairs of the examined hair sample and the calibration hair samples do not match.

The calibration model can be stored in a local memory of the assembly or in an external data storage unit. The detection unit records at least part of a spectrum of NIR light that has interacted with the hair sample and compares this spectrum with a plurality of calibration hair samples. For this adjustment, for example, a processor of the evaluation unit is used and at least a part of the spectrum of the examined hair sample is compared with the spectroscopic calibration model to determine the degree of elongation of the hair.

According to another version, the near-infrared sensor is a spectrometer, whereby the spectrometer is designed to generate a signal pattern based on the detected light, which is characteristic for the detected hair characteristics (can also be generally referred to as hair properties).

This means that it is not necessarily necessary to define absolute values for characteristics or properties of the hair. Rather, it may be sufficient to use the signal patterns obtained from the spectrometer to determine a product recommendation and/or application advice for the treatment and/or care of the hair. The signal pattern can be part of any calibration sample of the calibration model. Independently of this, it can be determined which products and/or application instructions are useful for hair samples with a specific signal pattern. The products and/or application instructions thus determined can then be assigned the corresponding signal pattern to express that these products and/or application instructions are suitable for hair with this signal pattern and to achieve a specific effect. This means that it is easier to find a suitable product recommendation because only the signal patterns detected in the hair sample examined need to be compared with signal patterns associated with the products and/or application and treatment instructions.

According to a further design form, the arrangement further comprises a housing and an energy storage unit, wherein the evaluation unit is accommodated in the housing and the detection unit is coupled to the housing, and wherein the energy storage unit is arranged in the housing in order to supply the evaluation unit with energy and in order to enable self-sufficient operation of the evaluation unit at least temporarily without connection to an external energy source.

This means that the evaluation unit can be operated autonomously and without external energy supply as intended. The energy store is preferably a rechargeable energy store. In one design example, the user interface is also located in the housing and can be supplied with power from the energy source, so that it can also be operated autonomously. In another design example, the energy storage unit can also supply the registration unit with energy.

The housing and the evaluation unit can be part of a user's personal device. The personal device can be a portable computer in the form of a smartphone, tablet, or other computer (these units can be commonly referred to as a computing unit or portable computing device). The acquisition unit can be connected to or integrated into the calculation unit and used to determine the degree of stretching of hair, as described herein. In a computer program product (e.g. software or application for the personal/portable device) the recorded characteristics of the hair are then displayed in the form of values, arbitrary units, or output acoustically. The parameters can then be used to (a) derive product recommendations for individually suitable treatment products and individual treatment tips and/or (b) determine and/or display the treatment success of a cosmetic treatment that aims to positively influence the measured parameters.

The registration unit can have an interface (also: data transmission connection) via which a connection to the computing unit is established. The computer unit can have a first interface and a second interface. The first interface can be designed as a counterpart to the interface of the acquisition unit, i.e. to connect the acquisition unit to the computing unit. The second interface can be designed to connect the computing unit to a data network. These connections are designed to transmit information in at least one direction, preferably in both directions. The connection between the recording unit and the computing unit on the one hand and the connection between the computing unit and an access point of the data network can be wired or wireless. Wired connections can, for example, use optical or electrical signals to transmit information. Wireless connections typically use electromagnetic waves for signal transmission, e.g. radio signals or even optical signals.

Protocols that work according to the principles of mesh networks can be used to connect the acquisition unit to the computer unit. For example, the thread protocol, which is based on IPv6, can be used for data transmission and for connecting the registration unit to the computing unit. The thread protocol is used to connect automated or semi-automated devices with each other, in this case for example the acquisition unit with the computing unit.

In an example, the acquisition unit can be structurally attached to the computing unit, or vice versa. This means that the detection unit is mechanically attached to the computing unit or a housing of the computing unit. For example, this can be achieved by tool-free installation via a reversible connection. In the attached position, the registration unit can be held relative to the calculation unit by employing a detachable force-locking or form-fit connection. The interfaces between the registration unit and the computing unit can be arranged in such a way that an electrical connection between the registration unit and the computing unit is automatically established or established in the plugged-on position.

The computing unit can execute an application (or program, hereinafter also referred to as computer program product) that receives or queries data from the acquisition unit. The data received or queried is used in the application to determine one or more output values. The data is processed and/or evaluated by the application according to the approaches described herein.

To run the application, processors (and one or more memory modules) of the computing unit can be used. However, the calculation unit can also be designed to outsource calculation steps for the execution of the application. For example, the application can transfer the data received from or requested by the acquisition unit to an external processing unit. Before the data is transferred to the external computing unit, it can be pre-processed.

The external computing unit can be located at a distance from the acquisition unit and the portable computing unit. The portable computing unit can be connected to the external computing unit via the data network, i.e. be in a communication link. The external computing unit can be a single computer or processor or a network of computers or processors. In a computer or processor network, the computing load can be distributed to the individual components of the network under different aspects. In addition to computing power, this computer network can also provide storage capacity for the users and hold data released or marked by the users. This reduces the amount of memory required in the portable computing unit. It is also made easier for the user to exchange a portable computing unit because no or almost no data is stored locally. The computer network can be designed as a group of intermeshed networked servers.

According to another version, the evaluation unit is designed to compare the characteristics of treatment products for the treatment of hair with the recorded hair characteristics and to determine an effect of the treatment products on the hair taking into account the recorded hair characteristics.

This means that the treatment products are selected and determined according to the hair properties or hair characteristics detected. These treatments can be displayed on the user interface, for example, or output in other ways.

According to another version, the evaluation unit is designed to transfer the captured hair characteristics to a data storage unit and to request information from the data storage unit about the treatment of the hair according to the captured hair characteristics.

These instructions can be general instructions (without reference to a specific treatment agent) concerning the treatment of hair, but they can also be instructions with reference to a specific treatment agent. The instructions may also include explanations of which behaviors influence which properties of the hair and how.

The data storage unit may contain information from studies and information from literature sources and/or scientific publications. The evaluation unit can be designed to display, output, or at least alert a user to an extract of this information, depending on the captured properties of the hair.

According to another version, the arrangement still has a user interface, and the evaluation unit is designed to instruct the user interface to output the instructions received for treating the hair.

The user interface can, for example, be a display of the portable computing unit, in particular a so-called touch screen, which enables contents to be displayed visually and user input to be received by touch.

According to another version, the evaluation unit is designed to request information from a user and to take this information additionally into account when requesting the data storage unit in order to obtain from the data storage unit characteristics of treatment products for the treatment of hair according to the information requested by the user.

The information requested can be collected by employing a predefined questionnaire, in which a statement by the user is given weight or is selected from one of several possible answers. The prescribed questionnaire can deal in particular with the user's habits and extraordinary stresses and strains, e.g. dietary habits, duration and quality of sleep, amount drunk, type of drinks, use of stimulants (e.g. nicotine, alcohol), professional and leisure activities (spending a lot of time outside buildings in all weathers, staying in the mountains, visiting a solarium). The age, gender and ethnicity of the users can also be queried and used to query the treatment product data store. The requested information can also refer to a desired or achievable property of the hair.

According to another version, the evaluation unit has a local memory, which is designed to store the data retrieved by the data storage unit, preferably persistently.

This means that the evaluation unit can perform its functions at least temporarily without having to rely on a permanent connection to the data storage unit but the data network. The retrieved data is stored in the local memory. The data are stored in the local memory in such a way that they are retained when the evaluation unit is switched off or put out of operation (persistent storage). It is possible that the evaluation unit will only call up data from the data storage unit that matches a current image or current properties of the hair. It is also possible to retrieve and locally save data that matches slightly changed properties of the hair based on the current state. It is therefore not necessary to retrieve all data from the data storage unit and store it in the local memory. Rather, it is possible to transfer specific data or information from the data storage unit to the local memory that matches the recorded condition of the hair.

According to a further embodiment, the evaluation unit is designed to store the captured hair features with a time stamp relating to the acquisition of the hair features in the local memory.

This makes it possible to observe and analyze changes in the hair over time. Thus, these changes can also be used to issue appropriate non-therapeutic treatment products and/or treatment instructions. It also allows the user to monitor the changes to determine the achievement or approximation of self-defined goals.

According to a further version, the evaluation unit is designed to store the captured hair characteristics over a longer period of time, comprising at least two processes of capturing the hair characteristics in the local memory and optionally to call up a development of the hair characteristics over a pre-defined period of time from the local memory and to instruct the output unit to display or output this development.

According to another version, the evaluation unit is designed to transfer the recorded hair characteristics to the data storage unit.

The captured and transmitted hair characteristics can be assigned to a code number or an identifier of a user in the data storage unit, so that a user can view his data from different devices. This procedure also has the advantage that a user's data is saved or stored at a central location in the event of loss or defect of the personal evaluation unit.

Furthermore, this design allows to record hair characteristics of a user over a longer period and to observe their changes and, if necessary, to link them to recommendations for non-therapeutic treatment agents and/or treatment instructions.

According to another version, the arrangement is designed to issue instructions for operating the registration unit visually on the output unit and/or acoustically via a loudspeaker. This can be particularly helpful when a user's hair is being recorded for the first time and comprehensively to gain an overview of the condition of the hair.

According to another version, the output unit is designed to output information about a treatment agent, e.g. a product name, information about ingredients and/or composition of a treatment agent and/or application instructions for non-therapeutic treatment of the hair.

This enables a user to form his or her own opinion about a treatment product in its entirety. In addition, the user can be given instructions for use related to a treatment product or independently of it. The application instructions can refer to desired and/or undesired behavior.

According to another version, the user interface is designed to receive an input from a user after the output of characteristics of a treatment agent and to initiate an action concerning the displayed or output treatment agent based on this input.

The action may, for example, relate to the user being offered a treatment product for sale and the user being able to initiate the purchase by employing an input. In addition to the purchase of treatment products, the user can also be offered more detailed information on the purchase. This more detailed information may refer to more detailed treatment and application instructions. For example, the program receives the request that the user wishes to purchase the treatment product, stores the request and/or transmits the request to a commercial company that distributes the treatment products. The user is requested by the computer program to enter his personal data (address, bank information, shipping preference, etc.) via the input unit.

Alternatively, the user can be dispensed where, for example in a drugstore, hairdressing salon, pharmacy, etc. in his vicinity, he can purchase the dispensed treatment product locally.

More and more customers want a product individually tailored to their needs. Accordingly, the user can be recommended an individually manufactured treatment product and an order process can be initiated, for example by calling up the website of a manufacturer of individual hair treatment products.

This may be a treatment product specially manufactured for one user or a so-called "mass customized" product. In the case of a "mass customized" product, individualization can be achieved by varying a few features of a product that are decisive from the customer's point of view. These "mass customized" products are preferably based on the concept of modularization, i.e. the product can be individually assembled from various modules/components.

There are often numerous interdependencies between the many different characteristics/ingredients of a product, which can be expressed as "commandments" or "prohibitions". To obtain a clear product definition, it can be advantageous to use a product configurator during the ordering process. This configurator helps the user to select the features/ingredients and draws his attention to the allowable/non-permissible combinations of features, the latter of which cannot then be selected.

In the case of hair treatment products, the relevant product characteristics include the chemical ingredients of the products, the physical properties of the products and the way in which the products are packaged. With the help of a product configurator, for example, the selection of chemically and/or physically incompatible ingredients or the selection for the determined degree of damage/strain/etc. of unsuitable ingredients can be avoided. Conversely, the selection for the determined degree of damage/strain/etc. of suitable ingredients can be specified or suggested by the product configurator.

It is also possible to produce an individual hair treatment product on site, i.e. for example in a hairdressing salon or at a point of sale of hair treatment products, such as a drugstore, using a mixing device, preferably a smart mixer.

According to another aspect, a method for determining a degree of stretching of hair is given. The procedure has the following steps: Irradiating a hair sample with electromagnetic waves in the infrared range; detecting the light emitted from the hair sample; detecting an absorbance of the hair sample in a wavelength range of from about 800 to about 2500 nm; generating an absorption spectrum of the hair sample in the wavelength range of from about 800 to about 2500 nm; matching the generated absorption spectrum with a calibration model; and determining the degree of elongation of hair based on the absorption spectrum and the calibration model.

This procedure corresponds to the function of the arrangement described above. The process steps correspond to the functions of the arrangement and are not described again here. In any case, for details on the process steps, please refer to the above description of the arrangement and its function. The other functions of the arrangement can of course also be implemented as process steps.

When matching the generated absorption spectrum with the calibration model, in particular a curve of the absorption spectrum of the hair sample can be matched with a plurality of absorption spectra from the calibration model.

According to an implementation form, the procedure has the following step: Detect or obtain a hair sample moisture level and use the hair sample moisture level to match the generated absorption spectrum to the calibration model.

According to an implementation form, the procedure has the following step: Assign a damage category to the hair sample based on matching the generated absorption spectrum to the calibration model.

According to another aspect, a method for determining a treatment agent based on the determined degree of stretching of hair is given. The procedure has the following steps: Using the determined degree of stretching of hair; selecting a treatment agent for hair based on the determined degree of stretching and outputting information about the selected treatment agent.

The treatment agent is selected or determined depending on the determined or specific degree of stretching and in consideration of a desired effect, for example desired properties of the hair after the treatment. The desired effect can be a user-defined effect or a desired condition of the hair. It may be helpful to assign to each treatment agent one or more types of damage or degree of elongation at which it can be applied, and also an effect that the treatment agent has at the corresponding type of damage or degree of elongation. In this way, a simple comparison of the type of damage or degree of elongation and the desired effect can be used to determine the appropriate treatment agent.

According to another aspect, a computer program product is specified which is designed to perform the procedure as described herein when executed on a device as also described herein.

The computer program product allows the control and follow-up of the results by displaying (e.g. graphically) the measurement results over time. Based on the results obtained, the computer program product provides individual treatment- and product tips. The quality of the treatment and product tips can be improved by the user answering additional questions about his hair condition, dietary habits, general health, and other behavior that the computer program product can process accordingly. This is based not only on e.g. literature data, but also on the treatment success of other users of the computer program product, especially treatment successes of other users who have at least a similar hair condition.

The data collected through the questionnaire can be used to analyze a development of the condition of the user's hair under the given circumstances, i.e. the data entered by the user. This development can be compared with the development of other users. From this, it can be concluded whether, during treatment with a given product, the evolution of users with similar or identical submissions in the questionnaire is similar or different from users with different submissions.

The data entered by the user can thus be used for a global analysis in order to monitor the success of a treatment and the effectiveness of a product under different conditions and, if necessary, recommend changes to the treatment and/or product.

BRIEF DESCRIPTION OF THE DRAWINGS

The present disclosure will hereinafter be described in conjunction with the following drawing figures, wherein like numerals denote like elements, and.

In the following, reference is made to the attached drawings which form part of the present application and which, for illustrative purposes, show specific embodiments in which the present disclosure can be exercised. It is understood that other embodiments may be used and structural or functional or logical modifications may be made without departing from the scope of protection of the present disclosure. In this respect, directional terminology such as "top", "bottom", "front", "back", "front", "rear", etc. is used with reference to the orientation of the figure(s) described. Since components of embodiments can be positioned in several different orientations, the terminology of directions is for illustrative purposes only and is in no way restrictive. It is understood that the characteristics of the various exemplary designs described herein may be combined, unless specifically stated otherwise. The following detailed description is therefore not to be understood in a restrictive sense and the scope of protection of the present disclosure is defined by the appended claims and equivalents thereof.

Figure 1:
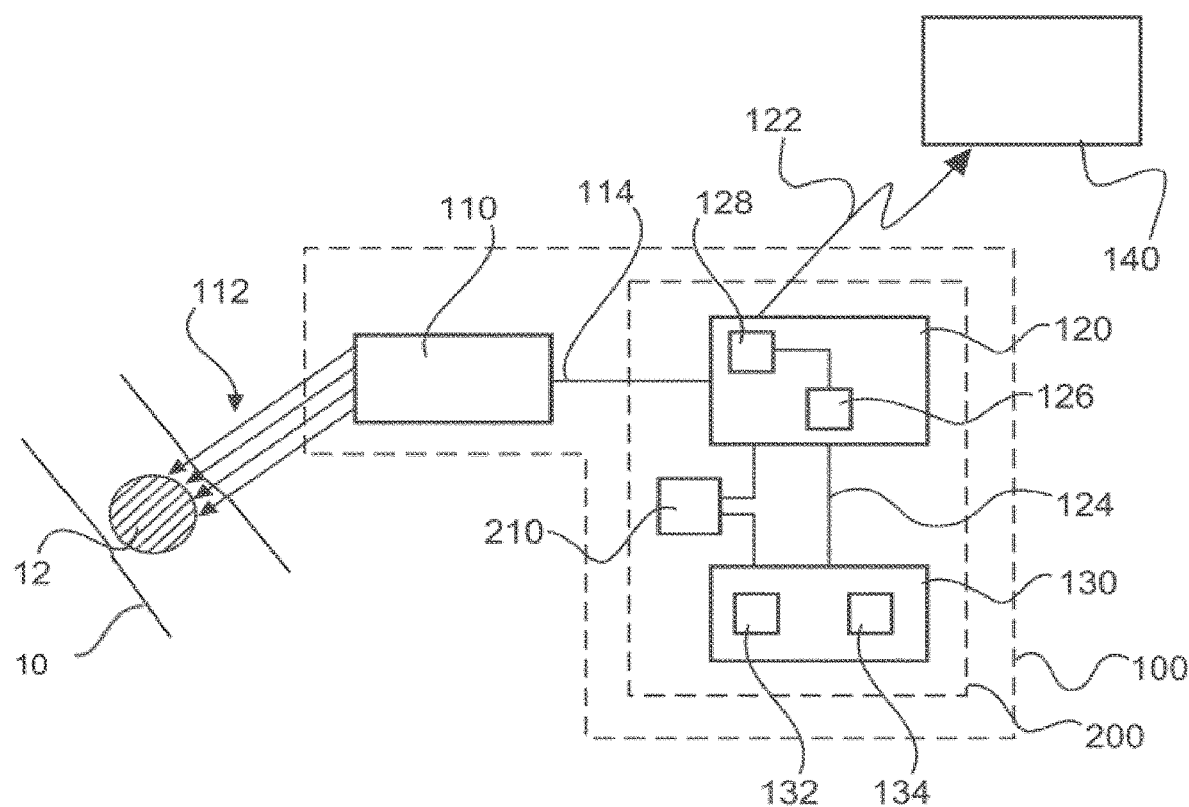
FIG. 1 is a schematic representation of an arrangement for determining a degree of stretching of hair according to an execution example.

FIG. 1 shows an arrangement 100 to determine a degree of stretching of hair. Arrangement 100 has an acquisition unit 110, an evaluation unit 120 and a user interface 130. The Acquisition Unit 110 is designed to acquire properties or characteristics of hair. For this purpose, the detection unit emits 110 infrared light in the direction of an area 12 of the analysis object 10 to be examined (e.g. of human hair) and detects the emitted light in order to detect an absorption coefficient of the hair sample in a wavelength range from about 800 to about 2500 nm. The light emitted from the area 12 to be examined is picked up by the detection unit 110 and allows conclusions to be drawn about the degree to which the hair is stretched, because the structure changed when the hair is stretched or overstretched has an individual absorption spectrum in the detected wavelength range.

The detection unit 110 has a suitable source of electromagnetic waves. This source is a light emitter or laser emitter, also known as a radiation source, and is located on or in the detection unit 110. The radiation source may be placed on or in the detection unit 110 in such a way that when the electromagnetic waves 112 are emitted, the radiation source occupies a predetermined distance from the area 12 to be examined, in particular when the detection unit 110 is placed on the area to be examined. The distance of the radiation source from the area to be examined can be variable and can be changed by actuators or manually.

The registration unit 110 is connected to the evaluation unit 120 via a data transmission connection 114. The data transmission connection 114 can enable unidirectional or bidirectional data transmission between the acquisition unit 110 and the evaluation unit 120. Thus, the detection unit 110 delivers signals concerning the detected characteristics of the hair to the evaluation unit 120, whereas the evaluation unit 120 can deliver control commands to the detection unit 110, whereby the control commands determine how the detection unit 110 operates. In the case of a unidirectional data transmission connection 114, which only allows data transmission from the acquisition unit 110 to the evaluation unit 120, control parameters can be specified via input elements (buttons, switches, rotary knobs, etc., not shown) on the acquisition unit 110. The registration unit 110 may have display elements (not shown) that indicate a status of the registration unit or the set control parameters. Alternatively, the registration unit 110 can also transmit the set control parameters to the evaluation unit 120, where they can be optionally displayed.

The evaluation unit 120 has a processor 126 and a local memory 128. The evaluation unit 120 receives signals concerning the characteristics of the examined area 12 of the hair sample 10 and determines a recommendation for a non-therapeutic treatment of the examined hair based on these characteristics. The non-therapeutic treatment may include recommendations on treatment products and/or treatment instructions or application instructions for the hair examined Treatment and application instructions are used as synonyms in the context of this description and refer to instructions for non-therapeutic treatment of the examined area (hair) 12 using selected treatment products or even without the use of treatment products. Treatment instructions may include the use of a treatment agent, or measures to be taken or not to be taken by the user. For example, the treatment instructions may include an indication of desirable or undesirable behavior after the use of a treatment product. To determine a non-therapeutic treatment to be recommended, the recorded characteristics of the investigated area 12 can be compared with areas of application, effects, and instructions for use of treatment agents and/or treatment instructions. Information on the treatment agents and/or treatment instructions can be stored in a data storage unit 140.

The data storage unit 140 can be located outside and spatially separated from the evaluation unit 120. The evaluation unit 120 can access the data storage unit 140 via a data network 122 and call up information on the treatment products stored there and/or treatment instructions. This retrieved information is compared by the evaluation unit 120 with the recorded characteristics of the examined area 12 to determine appropriate recommendations for the non-therapeutic treatment of the examined hair. In other words, this means that the data storage unit will be queried using the acquired hair characteristics (or determined hair properties). From the data storage unit, a large amount of stored information can first be retrieved and then filtered using the hair properties determined and, if necessary, treatment targets to determine which of the treatment agents and/or treatment instructions are relevant. For this purpose, the data can be loaded from the data memory into a volatile working memory. Alternatively, the determined hair properties can already be used when retrieving the information from the data memory to retrieve only the relevant information from the data memory. For the purposes of this description, these two variants can be considered equivalent in their effect.

The data network 122 may be a public data transmission network comprising sections of wire or wireless transmission. For example, the evaluation unit 120 may establish a wireless connection to an access point (not shown) to the data network 122 to establish a corresponding connection to the data storage unit 140.

The user interface 130 is connected to the evaluation unit 120 via the data transmission connection 124. The user interface 130 has an input unit 132 and an output unit 134. The input unit 132 enables a user to set parameters for the operation and configuration of the evaluation unit 120, the registration unit 110 and/or the user interface 130. Input unit 132 can record information via various interfaces: a keyboard, a mouse, a touch-sensitive display or via a microphone (so-called voice control). It is conceivable that any interface is used via which a human user can communicate with a computing unit and enter or transfer data. Use the input unit to enter the air humidity or a humidity level of the hair. The output unit 134 can be a display or other display unit that provides visual information to a user. The output unit 134 can also have a loudspeaker via which acoustic information can be output. Visual information can be output on a touch-sensitive output unit so that the output unit also allows a user to make entries.

The evaluation unit 120 has a processor 126 and a local memory 128. The processor 126 executes instructions to perform its intended function or functions. The local memory 128 can store the characteristics of the hair detected by the detection unit 110 or the associated signals or values.

It is a special aspect of this design example that the registration unit 110 can be operated with an evaluation unit 120 and a user interface 130, which are implemented in a portable device of a user or consumer. This makes it particularly easy to couple a registration unit 110, which provides advanced analysis and examination possibilities for the hair of a human user, with a portable computerized data processing device. The portable data processing device can be, for example, a smartphone or tablet and a home computer. The registration unit 110 can be mechanically, electrically, and signal-wise connected or coupled to the portable data processing device via a defined interface.

Figures 2, 3:
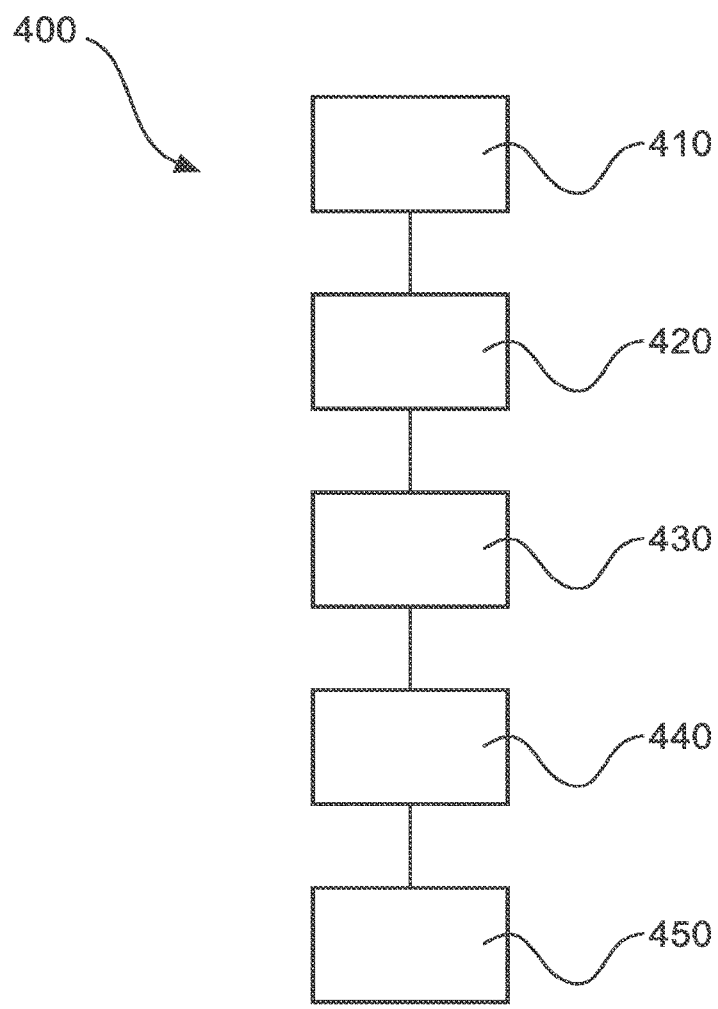
FIG. 2 is a schematic representation of a data carrier according to a further design example.
FIG. 3 is a schematic representation of the steps of a procedure according to a further execution example.

FIG. 2 shows a data carrier 300. A computer program product is stored on the data medium, which is designed to be executed on a portable computing unit 120 and to instruct a processor 126 of the portable computing unit to perform the following steps (cf. also the process steps in FIG. 3) Irradiating (410) a hair sample with electromagnetic waves in the infrared region; detecting (420) the light emitted from the hair sample; detecting (430) an absorbance of the hair sample in a wavelength range of 800 to 2500 nm; generating (440) an absorption spectrum of the hair sample in the wavelength range of 800 to 2500 nm; matching (450) the generated absorption spectrum with a calibration model and determining the degree of elongation of hair based on the absorption spectrum and the calibration model.

The 300 medium may use magnetic, optical, or electrical storage techniques (or combinations thereof) to hold the instructions of the computer program product in a machine-readable form. These instructions can be used to be executed directly by the processor 126 of a portable calculation unit 120 (the evaluation unit 120 from the execution example in FIG. 1). Alternatively, the instructions can be used to load the computer program product into an internal memory of the portable computing unit 120 for execution. This internal memory can be the local memory 128 shown in FIG. 1.

The data carrier 300 can be a mobile and/or portable data storage device. Alternatively, the computer program product can also be loaded via a data network by accessing the data carrier 300 from a portable computing unit via the data network in order to load the computer program product via the data network. The computer program product can be downloaded via a data network to a user's portable device and installed on the portable device for use by the user.

In addition to FIG. 2, FIG. 3 shows a procedure 400 with the following steps (these steps correspond to the functions of the computer program product): Irradiating (410) a hair sample with electromagnetic waves in the infrared region; detecting (420) the light emitted from the hair sample; detecting (430) an absorbance of the hair sample in a wavelength range of from about 800 to about 2500 nm; generating (440) an absorption spectrum of the hair sample in the wavelength range of from about 800 to about 2500 nm; matching (450) the generated absorption spectrum with a calibration model and determining the degree of elongation of hair based on the absorption spectrum and the calibration model.

The computer program product contains instructions that instruct the processor 126 of the portable calculator 120 to perform these steps 410 to 450.

Of course, the procedure 400 or its steps 410 to 450 can be modified in accordance with one of the execution examples of arrangement 100, as shown with reference to FIG. 1 and the other description. This means that the functions of arrangement 100 or one of its components described herein, the evaluation unit 120, can be implemented as step of procedure 400. It is not necessary to repeat the functions of the evaluation unit at this point. Rather, the expert will recognize that and how these functions are implemented as procedural steps.

The different process steps as well as the components of the arrangement can be realized by one or more circuits. In an embodiment, a "circuit" is to be understood as any entity that implements a logic, which may be hardware, software, firmware, or a combination thereof. Thus, a "circuit" in one embodiment may be a hard-wired logic circuit or a programmable logic circuit, such as a programmable processor, e.g. a microprocessor or a field programmable gate array (FPGA) device. A "circuit" can also be a processor that executes software, e.g. any kind of computer program, such as a computer program in programming code for a virtual machine (delimited runtime environment, virtual machine), such as a Java computer program. A "circuit" can be understood as any type of implementation of the functions described below.

Figure 4:
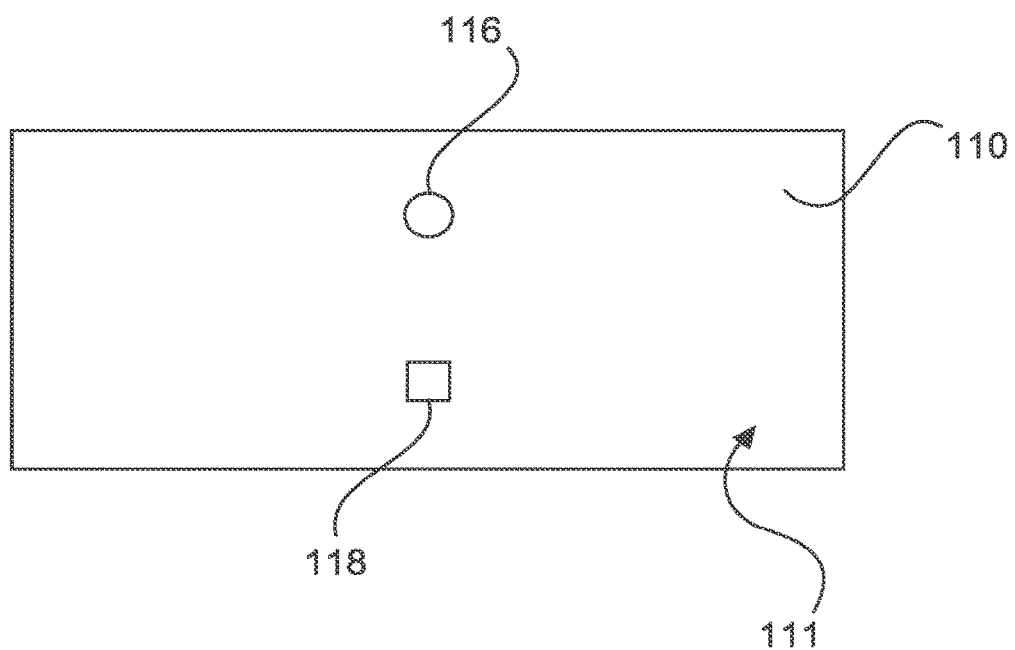
FIG. 4 is a schematic representation of an acquisition unit for an arrangement according to a further execution example.

FIG. 4 shows a schematic diagram of a registration unit 110. The detection unit has a surface 111 on which a light emitter 116 and a NIR sensor 118 are shown. The NIR sensor 118 can be a spectrometer. The light emitter 116 is shown circular and the NIR sensor 118 is shown square.

The surface visible from the detection unit 110 is that which faces the user's hair during a detection process. In other words, the light emitter 116 emits the light rays from the drawing plane towards an observer.

When the hair of a human user is irradiated with light (e.g. laser), part of this light is emitted depending on the chemical composition and/or structure of the hair.

The processor 126 (FIG. 1) can implement control functions and issue control commands to the light emitter 116. For example, the processor 126 can control the light emitter to emit light of a certain intensity, wavelength and/or spectral distribution (these can be called parameters of light).

The evaluation unit 120 with the processor 126 (FIG. 1) also receives the signals from the NIR sensor 118 and can classify the examined hair based on these signals. In other words, the signals delivered by the NIR sensor 118 are characteristic of the examined hair. These signals can also be called signal patterns and can be used to determine and output a product recommendation and/or application notes.

It is conceivable that a typical signal pattern is assigned to a product and/or an application note, where the product and/or the application note can be sensibly applied to the examined hair to achieve a desired treatment result. This assigned signal pattern of the products and/or application notes can be compared with the actual signal pattern from the detection unit. From a certain degree of conformity of the signal pattern detected or supplied by the spectrometer with the signal pattern assigned to the products and/or application notes, the corresponding products and/or application notes can then be issued. The signals can be examined for qualitative similarity (do the shapes or courses of the signals correspond) and/or quantitative similarity (do the signals have similar input values, i.e. light, similar output values, i.e. emitted light).

It is also conceivable that, depending on user input, a factor may be determined and applied to the signal detected by the spectrometer before this input signal is compared with the signal patterns of the products or application notes. This has the advantage that a correction factor can be applied to the acquired signal to improve the accuracy of product recommendations and/or application notes for a particular user.

Figure 5:
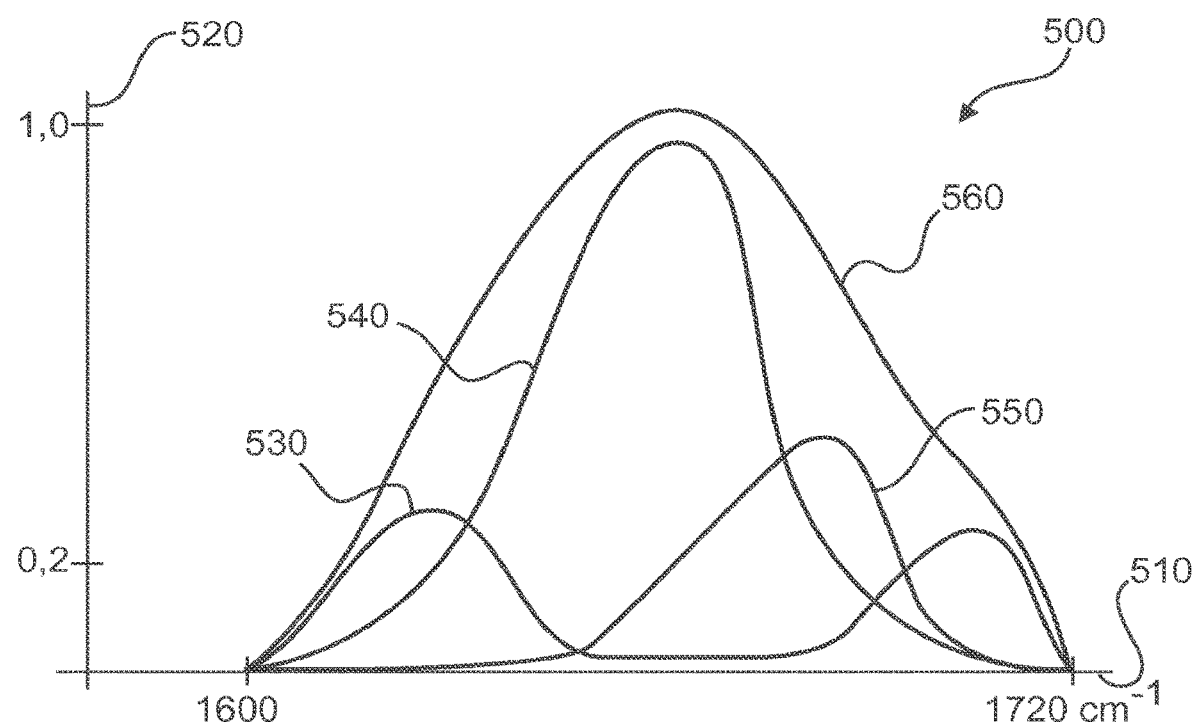
FIG. 5 is a schematic representation of an absorption spectrum characteristic of the degree of stretching of hair.

FIG. 5 shows an exemplary absorption diagram 500 in a wavenumber range from about 1600 $cm^{-1}$ to about 1720 $cm^{-1}$ (wavelength range between about 6250 nm and about 5813 nm). The wavelength range shown in FIG. 5 is above the NIR range (near infrared) and serves to understand the present disclosure. The displayed diagram shows the absorption spectrum of hair in a medium infrared wavelength range. On the horizontal axis 510 the wavenumber is plotted and on the vertical axis 520 an absorption coefficient measured as the proportion of absorbed light to emitted light (normalized to 1). In the mentioned wavenumber range, the absorption spectrum 530 of β leaflet structures, the absorption spectrum 540 of α helices, the absorption spectrum 550 of other randomly distributed protein fragments of the hair, and the resulting total absorption 560 is shown. The total absorption 560 results from the superposition of curves 530, 540 and 550. The qualitative shape and quantitative absorption values of curve 560 are characteristic of the degree of elongation of the hair sample.

However, measuring the absorption spectrum above the NIR range (above a wavelength of about 3000 nm) can be expensive. The present disclosure therefore proposes to use a near infrared sensor which detects an absorbance of a hair sample in a wavelength range between about 800 nm and about 2500 nm and generates the corresponding absorption spectrum. In the wavelength range between about 800 nm and about 2500 nm, between about 2000 and about 2500 nm, harmonics of α helices and β-leaf structures can be detected.

Figure 6:
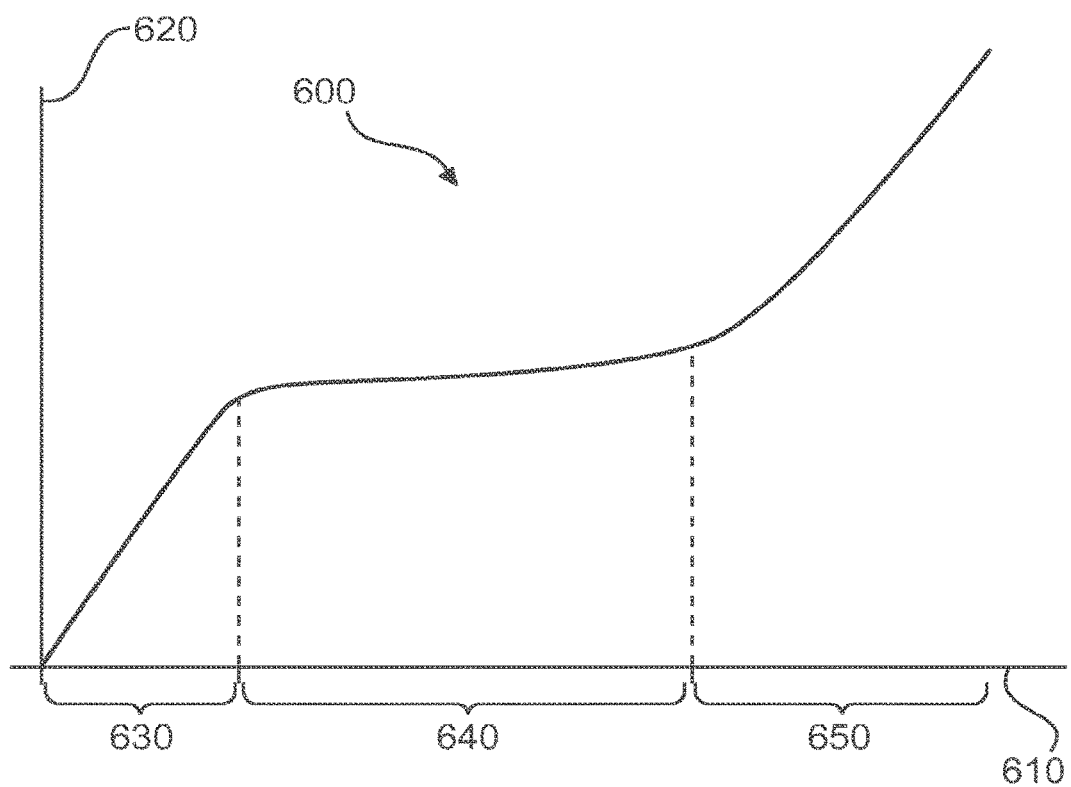
FIG. 6 is a schematic representation of a stress-strain diagram of hair.

FIG. 6 shows exemplary and qualitative a stress-strain diagram 600 for human hair. The horizontal axis 610 shows the elongation and the vertical axis 620 shows the tension in the hair.

In human hair, the stretching process is completely reversible up to about 3% to about 5% stretching (depending on the individual hair). This means that after relief, the hair returns to its original length before stretching. This range is marked with 630 and indicates the range of linear-elastic behavior. From approx. 10% to about 15% elongation, the irreversible transformation of α helices into β-pleated structures occurs. Due to the simple transformation of the secondary structures, this overstretching requires only small forces, as can be seen from a small or almost non-existent gradient of the curve in the 640 region. At about 25% elongation the hair tears.

However, this transformation of the hair is undesirable from a cosmetic point of view, as the hair in the transition area 640 clearly loses its mechanical stability.

Following the range 640 there is another range 650, which corresponds to a further increasing elongation. Here the tension continues to increase as the hair is stretched until it finally tears.

The analysis of the ratio of α helices to β-pleated structures is therefore, in addition to parameters such as oxidative damage, reductive damage, moisture, surface damage, another important variable for the holistic assessment of hair condition.

It has now been found that the described overstretching of hair can be easily determined using NIR sensors by comparing the absorption spectrum recorded with the NIR sensor with the absorption spectra of a calibration model, as described above. Due to its compactness and low cost, the process is also suitable for consumers, hairdressing salons and drugstores ("point of sale").

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An arrangement for determining a degree of elongation of hair, comprising:
    a detection unit for detecting hair characteristics; and
    an evaluation unit for evaluating the detected hair characteristics and for determining a degree of elongation of hair based on the detected hair characteristics,
    wherein the detection unit includes a near infrared sensor, NIRS,
    wherein the detection unit is configured to irradiate a hair sample with electromagnetic waves in the infrared region and to detect an absorbance of the hair sample in a wavelength range from about 800 to about 2500 nm,
    wherein the detection unit is configured to generate an absorption spectrum of the hair sample in the wavelength range from about 800 to about 2500 nm and to provide the absorption spectrum to the evaluation unit, and
    wherein the evaluation unit is configured to compare the absorption spectrum with a calibration model and to determine a degree of elongation of the hair sample based on the absorption spectrum and the calibration model.

2. The arrangement according to claim 1,
    wherein the evaluation unit is configured to compare a curve of the absorption spectrum of the hair sample with a plurality of absorption spectra from the calibration model.

3. The arrangement according to claim 1,
    wherein the detection unit is configured to detect or obtain a moisture level of the hair sample and provide the moisture level to the evaluation unit,
    wherein the evaluation unit is configured to consider the moisture content of the hair sample when comparing the absorption spectrum with the calibration model.

4. The arrangement according to claim 1,
    wherein the evaluation unit is configured to assign a damage category to the hair sample based on the comparison of the absorption spectrum with the calibration model.

5. The arrangement according to claim 1,
    wherein the near infrared sensor is a spectrometer, wherein the spectrometer is configured to generate a signal pattern based on the detected light that is characteristic of the detected hair features.

6. The arrangement according to claim 1,
    further comprising a housing and an energy storage device, wherein the evaluation unit is accommodated in the housing and the detection unit is coupled to the housing, and wherein the energy storage device is arranged in the housing and to supply the evaluation unit with energy and to enable at least temporarily a self-sufficient operation of the evaluation unit without connection to an external energy source.

7. The arrangement according to claim 1,
    wherein the evaluation unit is configured to compare the characteristics of treatment agents for treating hair with the detected hair characteristics and to determine an effect of the treatment agents on the hair including taking into account the detected hair characteristics.

8. The arrangement according to claim 1,
    wherein the evaluation unit is configured to transfer the detected hair characteristics to a data storage unit and to query from the data storage unit indications for the treatment of the hair according to the detected hair characteristics.

9. The arrangement according to claim 8,
    further comprising a user interface,
    wherein the evaluation unit is configured to instruct the user interface to output the hair treatment instructions received.

10. The arrangement according to claim 8,
    wherein the evaluation unit is configured to request information from a user and to additionally take the information into account when requesting the data storage unit to obtain from the data storage unit characteristics of treatment agents for treating hair in accordance with the information requested by the user.

11. A method for determining a degree of elongation of hair, comprising:
    irradiating a hair sample with electromagnetic waves in an infrared range;
    detecting the light emitted by the hair sample;
    measuring an absorbance of the hair sample in a wavelength range from about 800 to about 2500 nm;
    generating an absorption spectrum of the hair sample in a wavelength range from about 800 to about 2500 nm; and
    matching the absorption spectrum with a calibration model and determining the degree of elongation of hair based on the absorption spectrum and the calibration model.

12. The method according to claim 11, further comprising:
    detecting or maintaining a degree of moisture in the hair sample; and
    using a moisture content of the hair sample when comparing the absorption spectrum with the calibration model.

13. The method according to claim 11, further comprising:
    assigning a damage category to the hair sample based on matching the absorption spectrum to the calibration model.

14. A method for determining a treatment agent based on the degree of elongation of hair determined in claim 11, comprising the following steps:
    using a specific degree of stretching of hair; and
    selecting a treatment agent for hair based on the degree of stretching determined and outputting information about the treatment agent selected.

15. Computer program product configured to perform the method according to claim 11 when performed on an order according to claim 1.

* * * * *